US012245959B2

(12) United States Patent
Tuck et al.

(10) Patent No.: US 12,245,959 B2
(45) Date of Patent: *Mar. 11, 2025

(54) SYSTEM, DEVICE AND METHOD FOR ANCHORING A STENT

(71) Applicant: BOSTON SCIENTIFIC SCIMED, INC., Maple Grove, MN (US)

(72) Inventors: Daniel Tuck, Galway (IE); Martyn G. Folan, Galway (IE); Thomas M. Keating, Galway (IE); Martin Burke, Galway (IE)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/216,414

(22) Filed: Jun. 29, 2023

(65) Prior Publication Data
US 2023/0338174 A1    Oct. 26, 2023

Related U.S. Application Data

(63) Continuation of application No. 17/067,140, filed on Oct. 9, 2020, now Pat. No. 11,730,614.
(Continued)

(51) Int. Cl.
*A61F 2/04*  (2013.01)
*A61F 2/07*  (2013.01)
(Continued)

(52) U.S. Cl.
CPC .............. *A61F 2/848* (2013.01); *A61F 2/04* (2013.01); *A61F 2/07* (2013.01); *A61F 2/90* (2013.01);
(Continued)

(58) Field of Classification Search
CPC .... A61F 2/04; A61F 2/07; A61F 2/848; A61F 2/90; A61F 2220/0008; A61F 2002/044; A61F 2002/045
See application file for complete search history.

(56) References Cited

U.S. PATENT DOCUMENTS 5,667,523 A    9/1997  Bynon et al.
5,876,445 A    3/1999  Andersen et al.
(Continued)

FOREIGN PATENT DOCUMENTS

CN    103876868 A    6/2014
JP    2005500890 A    1/2005
(Continued)

OTHER PUBLICATIONS

International Search Report and Written Opinion for the International Patent Application No. PCT/US2020/055022, mailed Jan. 12, 2021, 13 pages.
(Continued)

*Primary Examiner* — Dinah Baria
(74) *Attorney, Agent, or Firm* — Seager, Tufte & Wickhem, LLP

(57) ABSTRACT

The present disclosure relates generally to stents, systems, and methods for anchoring devices within a body lumen by cooperation between the device and the body musculature. A device comprising an elongate tubular member may be deployed within a body lumen, where the body lumen includes a sphincter that regulates flow through the body lumen. The elongate tubular member includes a sleeve formed from a flexible membrane and one or more stents disposed at either or both ends of the sleeve. In some embodiments, the stents may be treatment stents configured to treat a portion of the body lumen. The elongate tubular member may be deployed within the body lumen such that the flexible membrane aligns with and moves in coordina- (Continued)

tion with the sphincter, thereby increasing retention forces acting upon the elongate tubular member when the sphincter is closed to minimize treatment stent migration.

20 Claims, 5 Drawing Sheets

Related U.S. Application Data

(60) Provisional application No. 62/915,051, filed on Oct. 15, 2019.

(51) Int. Cl.
*A61F 2/848* (2013.01)
*A61F 2/90* (2013.01)
*A61F 5/00* (2006.01)

(52) U.S. Cl.
CPC ...... *A61F 5/0079* (2013.01); *A61F 2002/044* (2013.01); *A61F 2220/0008* (2013.01)

(56) References Cited

U.S. PATENT DOCUMENTS

| | | |
|---|---|---|
| 6,264,689 B1 | 7/2001 | Colgan et al. |
| 6,283,992 B1 | 9/2001 | Hankh et al. |
| 6,585,758 B1 | 7/2003 | Chouinard et al. |
| 7,311,031 B2 | 12/2007 | McCullagh et al. |
| 8,211,186 B2 * | 7/2012 | Belhe .................... A61F 5/0079 623/23.65 |
| 9,517,122 B2 | 12/2016 | Firstenberg et al. |
| 9,801,749 B2 | 10/2017 | Hingston et al. |
| 10,052,220 B2 | 8/2018 | Ryan et al. |
| 10,130,502 B2 | 11/2018 | Chamorro et al. |
| 10,307,280 B2 | 6/2019 | Zeiner et al. |
| 10,420,665 B2 | 9/2019 | Sharma et al. |
| 10,548,753 B2 | 2/2020 | Rousseau |
| 10,682,220 B2 | 6/2020 | Folan et al. |
| 10,779,967 B2 | 9/2020 | Walsh et al. |
| 2003/0149472 A1 | 8/2003 | Pinchuk et al. |
| 2005/0085923 A1 | 4/2005 | Levine et al. |
| 2005/0131515 A1 | 6/2005 | Cully et al. |
| 2009/0210048 A1 | 8/2009 | Amplatz et al. |
| 2010/0106235 A1 | 4/2010 | Kariniemi et al. |
| 2010/0228335 A1 | 9/2010 | Schorgl et al. |
| 2010/0256775 A1 | 10/2010 | Belhe et al. |
| 2011/0087146 A1 | 4/2011 | Ryan et al. |
| 2011/0106273 A1 | 5/2011 | Belhe et al. |
| 2011/0270391 A1 | 11/2011 | Chitre et al. |
| 2011/0307070 A1 | 12/2011 | Clerc et al. |
| 2011/0319980 A1 | 12/2011 | Ryan |
| 2012/0065571 A1 | 3/2012 | Thompson et al. |
| 2012/0184893 A1 | 7/2012 | Thompson et al. |
| 2014/0121759 A1 | 5/2014 | Cully |
| 2014/0194805 A1 | 7/2014 | Levine et al. |
| 2014/0222039 A1 | 8/2014 | Khosrovaninejad |
| 2014/0243950 A1 | 8/2014 | Weiner |
| 2014/0277443 A1 | 9/2014 | Fleury et al. |
| 2014/0343683 A1 | 11/2014 | Jeon et al. |
| 2014/0350694 A1 | 11/2014 | Behan |
| 2015/0045908 A1 | 2/2015 | McMahon |
| 2015/0282922 A1 | 10/2015 | Hingston et al. |
| 2015/0374484 A1 | 12/2015 | Hingston et al. |
| 2016/0058914 A1 | 3/2016 | Bangera et al. |
| 2016/0081832 A1 | 3/2016 | Hingston et al. |
| 2016/0095724 A1 | 4/2016 | Harris et al. |
| 2016/0296317 A1 | 10/2016 | Timmermans et al. |
| 2017/0100332 A1 | 4/2017 | Tonkin et al. |
| 2017/0216543 A1 | 8/2017 | Magin et al. |
| 2017/0325983 A1 | 11/2017 | Valdes et al. |
| 2018/0036109 A1 | 2/2018 | Karavany et al. |
| 2018/0125630 A1 | 5/2018 | Hynes et al. |
| 2018/0250118 A1 | 9/2018 | Folan et al. |
| 2018/0280167 A1 | 10/2018 | Folan et al. |
| 2018/0360589 A1 | 12/2018 | Nolan et al. |

FOREIGN PATENT DOCUMENTS

| | | |
|---|---|---|
| JP | 2007513743 A | 5/2007 |
| JP | 2012506726 A | 3/2012 |
| JP | 2012519543 A | 8/2012 |
| JP | 2012522595 A | 9/2012 |
| JP | 20122522595 A | 9/2012 |
| JP | 2014521390 A | 8/2014 |
| JP | 2017527388 A | 9/2017 |
| KR | 2020130004575 U | 7/2013 |
| WO | 03020173 A1 | 3/2003 |
| WO | 2004049982 A2 | 6/2004 |
| WO | 2005058201 A1 | 6/2005 |
| WO | 2010051121 A1 | 5/2010 |
| WO | 2010101780 A2 | 9/2010 |
| WO | 2012128032 A1 | 9/2012 |
| WO | 2015195893 A1 | 12/2015 |

OTHER PUBLICATIONS

WallFlex™ Esophageal Stents—Full and Partially Covered Self Expanding Metal Stents—Boston Scientific product brochure © Oct. 2016.

Ultraflex™ Esophageal NG Stent System—Boston Scientific product brochure © May 2018.

Ultraflex™ Single-Use Tracheobronchial Stent System—Boston Scientific product brochure © Oct. 2014.

Goyal et al., "Physiology of Normal Esophageal Motility," Journal of Clinical Gastroenterology, vol. 42, No. 5, pp. 610-619, 2008.

Mittal, "Motor Function of the Pharynx, Esophagus, and its Sphincters," San Rafael (CA): Morgan & Claypool Life Sciences; Lower Esophageal Sphincter, 2011.

Hu et al., "Endoscopic stenting for post-transplant biliary stricture: usefulness of a novel removable covered metal stent." Journal of Hepato-Biliary-Pancreatic Sciences, vol. 18, pp. 640-645, 2011.

Davee et al., "Stent-in-Stent Technique for Removal of Embedded Partially Covered Self-Expanding Metal Stents," Surgical Endoscopy, vol. 30, pp. 2232-2242, 2016.

Hirdes et al., "Stent-in-Stent Technique for Removal of Embedded Esophageal Self-Expanding Metal Stents," vol. 30, American Journal of Gastroenterology, vol. 106, pp. 286-293, 2011.

Betzel et al., "Weight Reduction and Improvement in Diabetes by the Duodenal-Jejunal Bypass Liner:a 198 Cohort Study", Surgical Endoscopy, vol. 31, pp. 2881-2891, 2017.

Eisendrath et al., "Endotherapy Including Temporary Srenting of Fistulas of the Upper Gastrointestinal Tract after Laparoscopic Bariatric Surgery", Endoscopy vol. 39, pp. 625-630, 2017.

Muring et al., "Effectiveness of Endoscopic Management Using Self-Expendable Metalpost-Bariatric Leaks Stents in a Large Cohort of Patients with Post-Bariatric Leaks", Obesity Surgery, 8 pages, 2015.

Ge et al., "EUS-Guided Gastrojejunostomy with Lumen Apposing Metal Stent versus Enteral Stent Placement for Palliation of Malignant Gastric Outlet Obstruction", Gastrointestinal Endoscopy, vol. 87, No. 6S, 1 page, 2018.

Rebibo et al., "Combined Stents for the Treatment of Large Gastric Fistulas or Stenosis after Sleeve Gastrectomy", Endoscopy, vol. 47, E59-E60, 2015.

Van Boeckel et al., "Refractory Esophageal Strictures: What to Do When Dilation Fails", Esophagus, vol. 13, pp. 47-58, 2015.

Deviere et al., "Effectiveness of Endoscopic Management Using Self-Expandable Metal Stents in a Large Cohort of Patients with Post-Bariatric Leaks," Obesity Surgery, vol. 25, pp. 1569-1576, 2015.

* cited by examiner

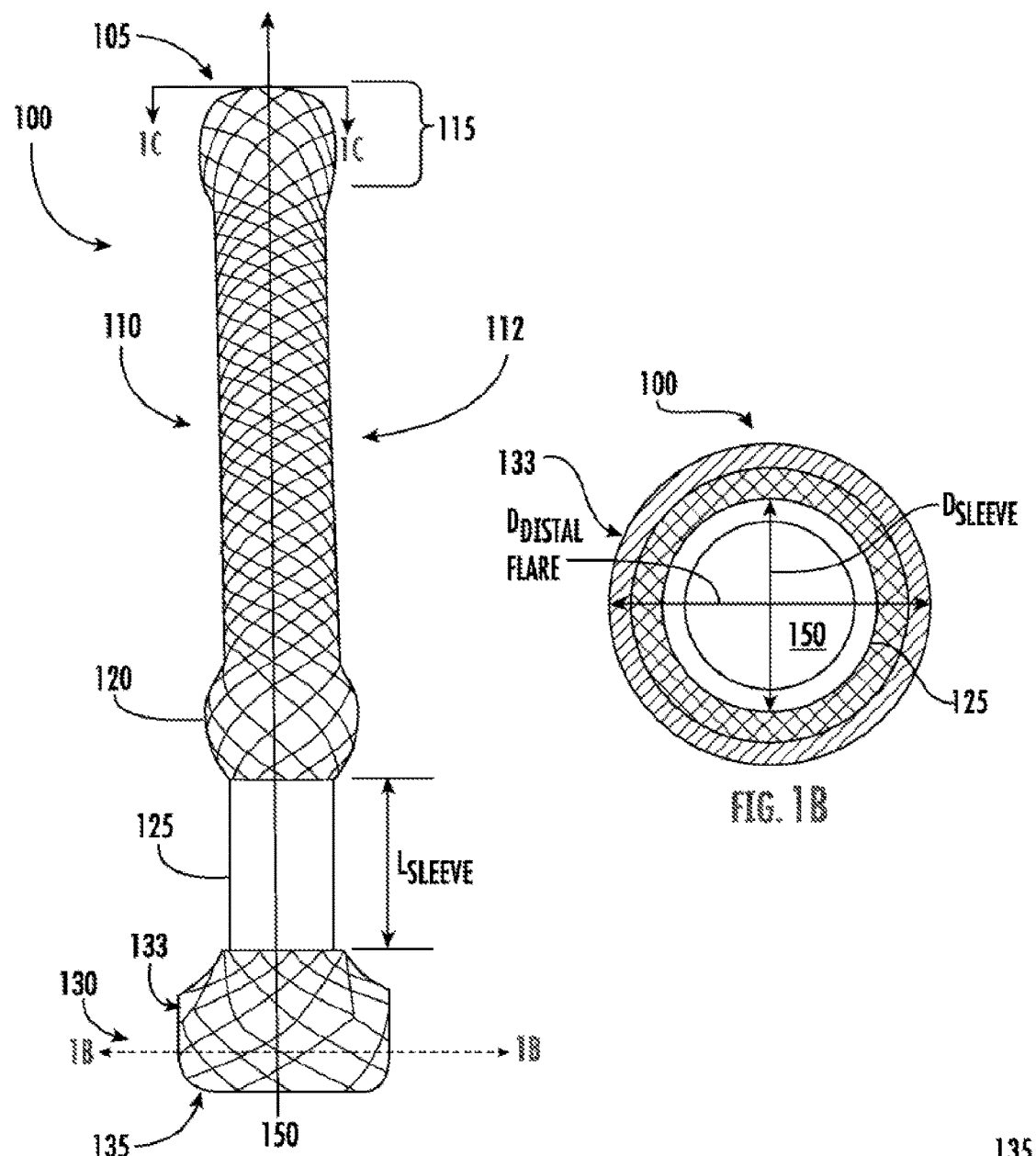
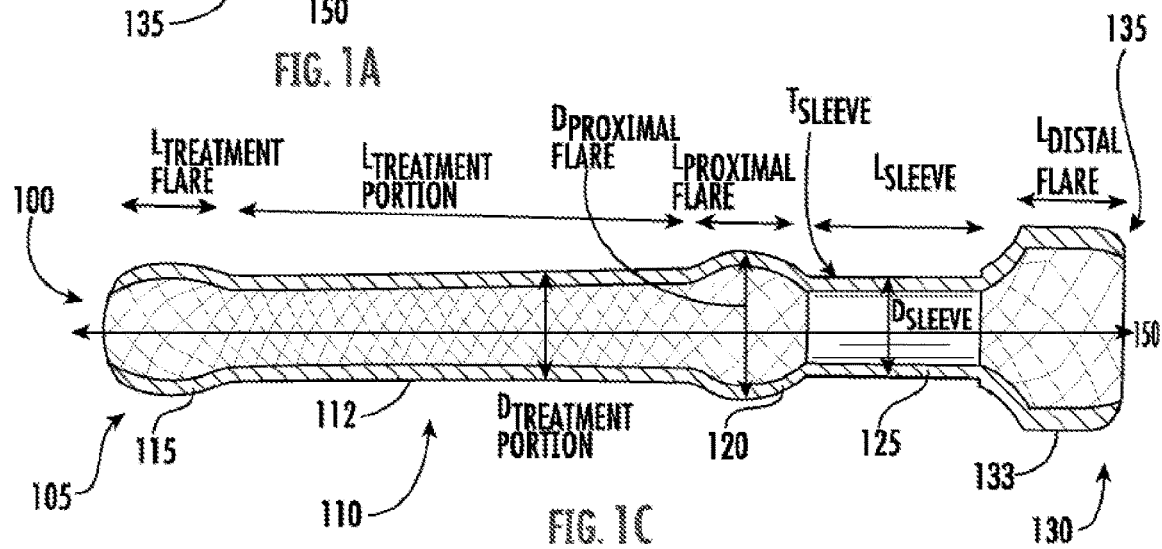

SYSTEM, DEVICE AND METHOD FOR ANCHORING A STENT

CROSS REFERENCE TO RELATED APPLICATIONS

The present application is a continuation of and claims the benefit of the earlier filing date of U.S. patent application Ser. No. 17/067,140, filed Oct. 9, 2020, which claims the benefit of priority under 35 U.S.C. § 119 to U.S. Provisional Patent Application Ser. No. 62/915,051, filed on Oct. 15, 2019, which applications are hereby incorporated by reference herein in their entireties for all purposes.

FIELD

The present disclosure relates to implantable medical devices and, more particularly, to stents, systems, and methods for esophageal and/or gastrointestinal tract treatment.

BACKGROUND

Persistent Esophageal Dysphagia (difficulty swallowing) may be caused by esophageal strictures which narrow or tighten tissue of the esophagus, thereby reducing the diameter of the esophageal passageway. An esophageal stricture may be caused by regurgitation of stomach acids and other irritants into the esophagus, resulting in inflammation and scar tissue buildup that, over time, can narrow the esophageal passageway and lead to weight loss, malnutrition and/or dehydration.

Treatment of esophageal strictures may involve non-invasive treatments like balloon dilation, wherein a balloon is deployed proximate to the stricture and inflated to stretch the stricture to open the esophagus. Generally, this treatment must be repeated at regular intervals in multiple procedures. Alternatively, expandable esophageal stents may be used to provide a pathway for food or other fluid to flow therethrough. Esophageal stenting involves inserting a braided stent into the esophagus to restore the esophageal anatomy.

One problem with esophageal stenting arises because the chronic peristaltic action of the esophageal muscles that moves food and liquid to the stomach region may cause the stent to migrate away from the treatment site, reducing treatment efficacy.

SUMMARY

The present disclosure in its various embodiments relates generally to stents, systems, and methods which may be used to address gastrointestinal issues. In particular, the present disclosure relates to a gastrointestinal treatment device including an elongate tubular body configured to leverage retention forces of body lumens, including sphincters, to reduce the potential for stent migration during chronic use.

According to one aspect, a device includes an elongate tubular body for use in a body lumen, the body lumen including a constriction portion that regulates flow between a first flow path and a second flow path. The device also includes a stent having a proximal end and a distal end and a sleeve, coupled to the stent and formed of a flexible membrane, where the sleeve is configured to transition between an expanded configuration enabling flow through the sleeve and a constricted configuration where flow through the sleeve is restricted. The stent and the sleeve together define a central lumen providing a flow path through the elongate tubular body.

In various embodiments, the stent may include at least one flare having a flare diameter that exceeds an expanded sleeve diameter, a stent diameter or both. The stent may be one of a plurality of stents including a proximal stent coupled to a proximal end of the sleeve and a distal stent coupled to the distal end of the sleeve. The proximal stent, the distal stent or both may include at least one flare. The device may include a proximal flare formed by the proximal stent and coupled to a proximal end of the sleeve and a distal flare formed by the distal stent and coupled to a distal end of the sleeve. The length of the sleeve may be related to an axial length of the constriction portion of the body lumen, the proximal flare may be configured to affix to tissue of the body lumen in the first flow path and the distal flare may be configured to affix to tissue of the body lumen in the second flow path. The stent may include a plurality of flares, where at least two of the plurality of flares differ in diameter. The flexible membrane may be comprised of a material configured to transition between the expanded configuration and the constricted configuration in response to forces provided by the constriction portion of the body lumen. The constriction portion of the body lumen may be a sphincter, the stent may be one of a plurality of stents and the sleeve may be configured to transition between the expanded configuration when the sphincter is opened to the constricted configuration when the sphincter is closed. The sphincter may be, for example, an esophageal sphincter, a hepatopancreatic sphincter, Ileocecal valve or a pyloric sphincter. The stent may be formed of a metal, a metal alloy, a polymer, a metal-polymer composite, a ceramic, or a combination thereof. The flexible membrane may be comprised of silicone. The sleeve may comprise a tube having one of a fixed or variable thickness, ranging from between 20 microns and 150 microns. The stent may include a treatment portion including one of a tubular scaffold, a coating, a mesh or combination thereof.

According to another aspect, a system includes a pair of elongate bodies, a first elongate body configured for affixation within a first body lumen, a second elongate body configured for affixation within a second body lumen, the first body lumen and the second body lumen each including sphincter regulated flow paths. The system includes a bypass sleeve, coupling the first elongate body to the second elongate body. Each elongate body includes a stent having a proximal end and a distal end and a sleeve, coupled to the stent and formed of a flexible membrane, where the sleeve is configured to transition between an expanded configuration enabling flow through the sleeve and a constricted configuration where flow through the sleeve is restricted. The sleeves cooperate with the sphincter regulated flow paths and stents to retain the bypass sleeve between the pair of elongate bodies.

In various embodiments, the sphincter regulated flow paths include an esophageal sphincter and a pyloric sphincter. The stent of one or both of the first elongate body or the second elongate body may include a flared portion having a diameter that exceeds the diameter of the stent. The flexible membrane may be comprised of silicone.

According to a further aspect, a method of anchoring a stent using a feature of a body lumen includes the steps of: deploying an elongate structure into a body lumen that couples a first organ to a second organ, where at least a portion of the body lumen is configured to constrict and expand, the elongate structure including a flexible sleeve configured to inhibit affixation of the flexible sleeve with tissue of the body lumen, and at least one stent coupled to the flexible sleeve and configured to affix to the body lumen by: releasing the at least one stent from a delivery catheter to a location proximate to the portion of the body lumen that constricts and expands; and releasing the flexible sleeve from the delivery catheter to align the flexible sleeve with the portion of the body lumen that constricts and expands enabling retention of the elongate structure within the body lumen by constriction of the body lumen.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures:

FIGS. 1A-1C are perspective views of a treatment device according to embodiments of the present disclosure;

DETAILED DESCRIPTION

Figure 2:
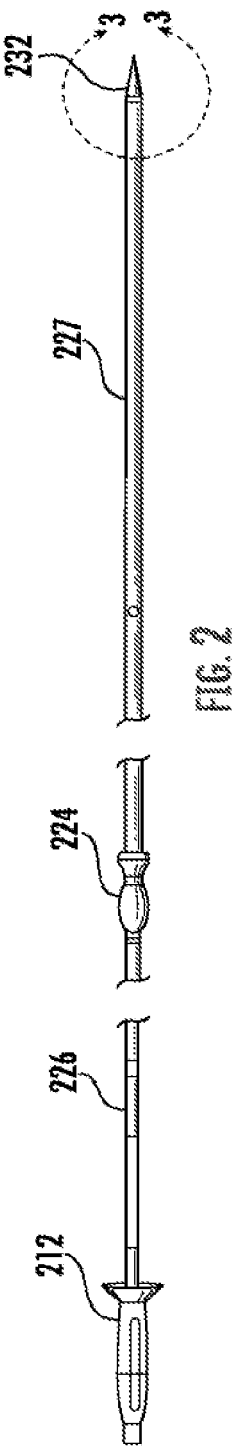
FIG. 2 depicts one embodiment of a delivery system that may be used to deliver the treatment device of FIGS. 1A-1C to a target treatment site, according to embodiments of the present disclosure.

The present disclosure is not limited to the particular embodiments described herein. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

According to one aspect, a treatment device may be anchored within a body lumen by leveraging a constriction mechanism of the body lumen to retain the treatment device. For example, the constriction mechanism of the body lumen may comprise a sphincter and the treatment device may include a flexible sleeve configured to move in coordination with the sphincter to anchor the treatment device and regulate a flow path through the sleeve. The flexible properties of the sleeve may reduce interference between the sleeve and the sphincter to maintain sphincter efficacy. When closed, the sphincter applies a retention force to the sleeve, thereby anchoring the treatment device and reducing the effect of peristaltic forces and the potential for treatment device migration.

These and other beneficial aspects of a treatment device including an anchoring mechanism are described below. It should be noted that although embodiments of the present disclosure may be described with specific reference to gastrointestinal sphincters, the principles disclosed herein may be readily adapted in any body lumen where constriction forces may be leveraged for anchoring purposes.

As used herein, the term "distal" refers to the end farthest away from the medical professional when introducing a medical device into a patient, while the term "proximal" refers to the end closest to the medical professional when introducing a medical device into a patient.

FIGS. 1A-1C illustrate perspective views of one embodiment of a treatment device 100 as disclosed herein. FIG. 1A is a side view of the treatment device 100 comprising an elongate tubular body having a proximal end 105 and a distal end 135. The treatment device 100 is shown to include a proximal stent 110 and a distal stent 130 coupled by a flexible sleeve 125. A central lumen 150 extends through the proximal stent 110, sleeve 125 and distal stent 130. Although both a proximal stent 110 and a distal stent 130 are shown, tissue treatment devices having either or both a proximal or distal stent are considered within the scope of this disclosure.

In one application, the treatment device 100 may be positioned within a body lumen with one or both of the proximal stent 110 or distal stent 130 disposed at a target treatment site and the flexible sleeve 125 disposed across a constriction feature of the body lumen, such as a sphincter. The flexible sleeve 125 is configured to move in coordination with the sphincter, which compresses and anchors the sleeve 125 (and thus the treatment device 100) when in a closed position. Anchoring the sleeve 125 in this manner secures the treatment device against migratory forces resulting from the peristaltic motion of the body lumen, thereby improving treatment device retention and efficacy. Additional anchoring of the treatment device 100 may be provided by flares extending radially from the elongate body, such as a proximal flare 120, a distal flare 133 and a treatment flare 115. In one embodiment, the treatment flare 115 may assist in retaining a treatment portion 112 of the elongate tubular body proximate to a treatment site. The proximal flare 120 and distal flare 133 may assist in retaining the sleeve 125 within the sphincter, utilizing body lumen musculature to further assist in retaining the treatment portion 112 of the treatment device 100 proximate to the treatment site. It is appreciated that the shape of the flares 120, 133 is selected based upon the shape of the body lumen and/or purpose of the flare. For example, flare 120 comprises a more rounded, bulb shaped flare which provides sufficient retention for use in an esophageal passageway without discomfort or obstruction, while flare 133 includes a flare which is more angular and wider, providing improved retention for the device 100 for retention in the stomach, below the esophageal sphincter, as described in more detail later herein.

Treatment devices such as those disclosed herein may be a part of systems and methods for treatment of GI tract diseases for a consistent, repeatable approach for anti-migration to treat the myriad of underlying conditions. As described above, the treatment device may include one or more stents. Each of the one or more stents may include a tubular scaffold having a first end opposite a second end, wherein a lumen extends between the first and second ends. In one embodiment, one or both of the proximal stent or distal stent may comprise self-expanding metal stents (SEMS) such as those used extensively in a minimally invasive manner throughout the gastrointestinal (GI) tract for the treatment of a myriad of disease states including, but not limited to, vessel lumen closure (e.g., stricture due to tumorous growth, surgical etiologies, etc.) and GI bypass complications (e.g., post bariatric leak treatments). SEMS may be removable or permanent, dependent on the disease state under treatment, with removability typically defined by the presence or absence of a durable coating. Permanent SEMS may not have a coating, which when placed within the GI tract, allows for vessel tissue ingrowth due to stimulated hyperplasia of the vessel. Eventually the SEMS is embedded in place as a result of the tissue ingrowth.

In some embodiments, one or both of the proximal or distal stents may be balloon or self-expanding. Self-expanding stent examples may include stents having one or more strut members combined to form a rigid and/or semi-rigid stent structure. For example, the strut members may be one or more wires or filaments which are braided, wrapped, intertwined, interwoven, weaved, knitted, looped (e.g., bobbinet-style) or the like to form the scaffold. Alternatively, the stent may be a monolithic structure formed from a cylindrical tubular member, such as a single, cylindrical tubular laser-cut Nitinol tubular member, in which the remaining portions of the tubular member form the strut members. Openings or interstices through a wall of the stent may be defined between adjacent the strut members.

The stent may be constructed from a variety of non-limiting materials. For example, when balloon or self-expandable, the stent may be constructed from a metal (e.g., Nitinol, Elgiloy, stainless steel, cobalt-chrome, positive temperature co-efficient of resistivity, etc.). In other examples, the stent may be constructed from a polymeric material (e.g., polyethylene terephthalate, poly (methyl methacrylate)). In yet other examples, the stent may be constructed from a combination of metallic and polymeric materials. In still yet other examples, the stent may include a bioabsorbable and/or biodegradable material (e.g., a poly (lactic-co-glycolic acid) polymer). Additional embodiments and materials that may be used to form the proximal and/or distal stent are provided later herein.

In one embodiment, the sleeve 125 may be formed of a flexible polymer, such as silicone. In some embodiments, the elongate tubular body is formed by shaping one or more spaced apart stents on a mandrel and coating the spaced apart stents with a silicone material, producing a sleeve 125 in the spaced apart area between the stents. In some embodiments, the sleeve comprises a solid silicone cylinder. In other embodiments, the sleeve may have openings (slits, slots, etc.) to facilitate movement of the sleeve. The present disclosure is not limited to sleeves formed of silicone and other flexible materials, including but not limited to, PTFE, ETFE, FEP<PolyUrathane, PVC, Polyether-ester (e.g. ARNITEL®), PEBAX, PE, PEEK, PFA, PVDF, Chronoflex, Marlex and composites of the above.

As mentioned above, each of the stents may include one or more flares configured to assist with retention of the treatment device 100 at a desired treatment site. In general, the diameter, axial length and shape of a flare is selected to assist with retention of the treatment device by musculature on either side of the sphincter without interference with the organ in which it is disposed. Each flare generally has a larger diameter than the neighboring stent and/or sleeve. For example, in exemplary esophageal treatment devices, the diameter of the proximal stent may range between 14 mm and 25 mm, and the diameter of the flares may increase the diameter by 3-5 mm.

FIG. 1B is a cross section of the treatment device 100 taken along line 1B-1B of FIG. 1A. The diameter $D_{DISTAL\ FLARE}$, which corresponds to the diameter of the distal flare 133 of the distal stent 130, exceeds the diameter $D_{SLEEVE}$ of the sleeve 125. As such, the distal flare acts to secure the sleeve 125 across the constrictive portion of the body lumen during use.

FIG. 1C is a cross section view of the treatment device 100 taken along line 1C-1C of FIG. 1A. As shown in FIG. 1C, similar to the distal flare 133, the diameter $D_{PROXIMAL\ FLARE}$ of proximal flare 120 exceeds the diameter of the $D_{SLEEVE}$ of the sleeve 125 as well as the diameter $D_{TREATMENT\ PORTION}$ of the treatment portion 112 of the proximal stent 110. With such an arrangement, the proximal flare 120 may help to retain the position of the proximal stent 110 and the sleeve 125 during use.

It is appreciated that the axial length, diameter, shape, number and spacing of features of a treatment device, including the treatment portion 112, sleeve 125 and flare 133, 120, 115 may be selected as a function of a location, type or extent of treatment intended to be provided by the treatment device. Herein, the "axial length" means the length of a feature taken along an axis defined by the central lumen 150 extending from the proximal end 105 to the distal end 135 of the treatment device. For example, a treatment device 100 for use in esophageal stenting may have a treatment portion 112 with an axial length $L_{TREATMENT\ PORTION}$ selected based on patient anatomy, for example ranging from 16 mm-150 mm. The size, shape, spacing and extent of the flares 115, 120, and 133 may be customized according to the particular organ in which the treatment device is intended to be disposed.

For example, the treatment device 100 includes an esophageal stent treatment portion 112 and flare 115 that may be anchored within the esophagus by the flares 115 and 120. Further anchoring assist is provided by the sleeve 125, which may be disposed across the lower esophageal sphincter (LES). In such an embodiment, an axial length $L_{sleeve}$ of the sleeve 125 may be selected based on the anatomy of the LES to enable the sleeve to be constricted within the sphincter while leaving the proximal stent 110 and distal stent 130 exposed to organ tissue adjoining the sphincter, allowing the flares 120, 133 to engage tissue without being pulled into and interfering with the operation of the sphincter. For example, in various embodiments, the length of the sleeve $L_{SLEEVE}$ for use across an LES may range from about 2 cm to about 8 cm.

An axial length $L_{PROXIMAL\ FLARE}$, shape and diameter of the proximal flare 120 may be optimized for affixation with the esophagus, while the axial length $L_{DISTAL\ FLARE}$, shape and diameter of the distal flare 133 may be optimized for affixation with the stomach. Thus, as shown in FIG. 1C, the diameter of the distal flare 133 is larger than that of proximal flare 120, to provide retention of the device within the larger stomach organ as opposed to a narrower esophageal passageway. The shape and slope of the flare 133 is further selected to provide optimum retention based on the stomach anatomy, and thus comprises a different shape and size that the proximal flare 120. The length $L_{TREATMENT\ FLARE}$, diameter and shape of treatment flare 115 is further optimized for its intended purpose; e.g. retaining the treatment portion 112 of the proximal stent 110 in a desired location within the esophagus.

Sleeve 125 is formed from a flexible material having a thickness T SLEEVE. As discussed above, in one embodiment, the sleeve 125 may be formed of a flexible polymer such as silicone. The silicone sleeve may be formed by coating (e.g., dipping, spraying, etc.) a mandrel, upon which the proximal and/or distal stents are disposed, with silicone or another flexible polymer. In one embodiment, as shown in FIGS. 1A-1C, the coating may be evenly applied along the entire length of the treatment device, creating the sleeve between the distal stent 130 and proximal stent 110. In alternate embodiments, the coating may be unevenly applied, across the device, for example increasing in thickness proximally or distally, forming external ridges, or covering only part of the body. In other embodiments, the sleeve may be formed separately from the one or more stents and glued or otherwise connected to the stents. In some embodiments, the thickness of the sleeve may range from between 40-100 microns for dipped processes, and between 20-150 microns for spray processes.

Figure 3:
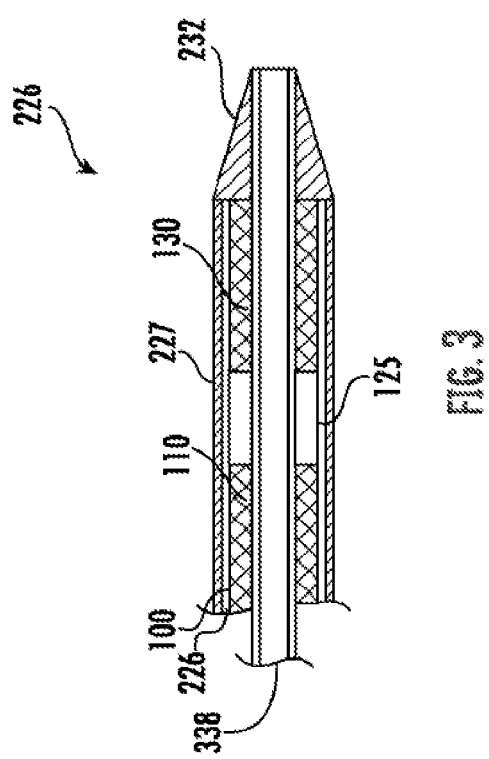
FIG. 3 is a cross sectional view of a distal tip of a delivery catheter of one embodiment, carrying a treatment device as disclosed in embodiments of the present disclosure.

FIG. 2 and FIG. 3 illustrate an exemplary delivery system that may be used to deliver a treatment device such as that described in FIGS. 1A-1C to a treatment site and the figures will be used together to describe one exemplary method of delivery. The delivery system includes an outer sheath 227 comprising a coupler 224 for slideably accepting an inner sheath 226 configured to carrying a stent within its distal tip 232 for delivery of the stent to a treatment site. A control handle 212 may be used by a surgeon to deploy the implant, for example by translating the handle 212 towards the coupler 224 to advance the inner sheath 226 within the outer sheath 227 to thereby release the treatment device from the distal tip 232.

FIG. 3 is a cross section view of the distal tip 232 of the delivery catheter prior to delivery of the treatment device 100 to a treatment site. In FIG. 3, the inner sheath 226 has been advance through the outer sheath 227 to position the treatment device 100 at the distal tip 232. A shaft 338, internal to the inner sheath may be provided to expel the treatment device through the distal tip 232 of the outer sheath 227.

Delivering the treatment device to the treatment site may be performed by advancing the distal tip of a delivery catheter (comprising the outer sheath 227, inner sheath 226 and treatment device 100) over a guidewire to the treatment location. The distal end 232 of the delivery catheter may be positioned via trans-oral entry adjacent to a target location within the GI tract, for example a distal end or proximal end of a sphincter. The distal stent 130 may be released by advancing handle 212 distally to a predetermined position to first expel the distal stent 130. Further distal translation of the inner sheath may enable the sleeve 125 to be disposed across the sphincter. Accuracy of placement of the sleeve across the sphincter may be determined using visualization techniques, or by tensile feedback, for example by feeling the resistance of the distal flare against the sphincter opening. Once it is determined that the sleeve is appropriately positioned within the sphincter, the proximal flare may be released for positioning proximate the treatment site.

Figure 4:
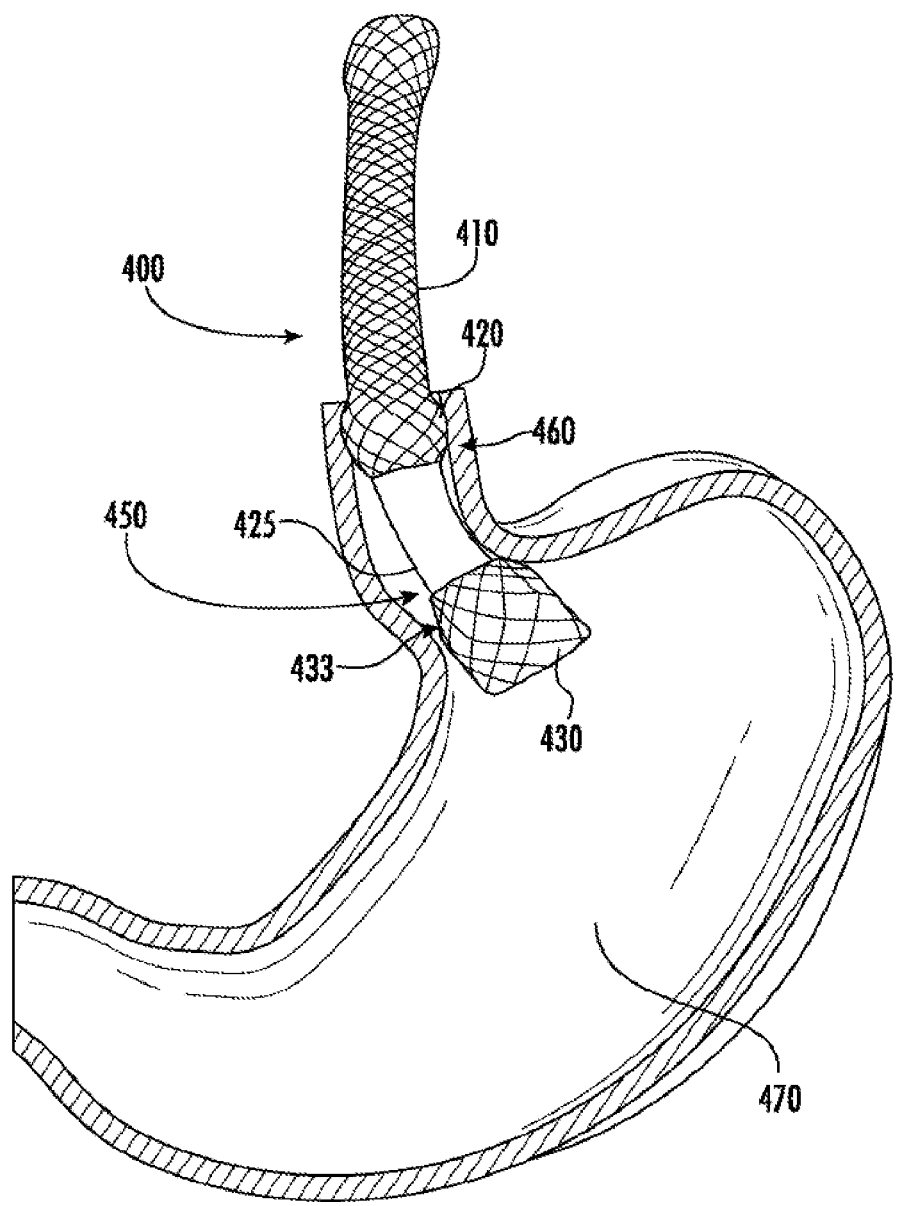
FIG. 4 illustrates one embodiment of a treatment device following deployment across a lower esophageal sphincter.

FIG. 4 illustrates an exemplary embodiment of a treatment device 400 deployed across a lower esophageal sphincter. The treatment device 400 is similar to the device of FIGS. 1A and 1s shown to include an elongate tubular body comprising a proximal stent 410, a distal stent 430 and a flexible sleeve 425 disposed between the proximal stent 410 and the distal stent 430. A proximal flare 420 is disposed at a distal end of the proximal stent 410 within the esophagus 460, retaining the proximal stent 410 within the esophageal passageway. A distal flare 433 of the distal stent 430 is disposed within the stomach, cooperating with the proximal flare 420 to anchor the sleeve 425 across the lower esophageal sphincter 450. With such an arrangement, the treatment device may use the musculature of the body lumen (e.g. the sphincter) to provide an additional anchoring mechanism to diminish the potential of migration of the treatment device that may otherwise occur due to the peristaltic forces of the digestive tract.

A treatment device including an LES anchor such as that illustrated in FIG. 4 may be used in a variety of medical applications. For example, the device may improve the efficacy of esophageal stenting by reducing the potential for device migration. Alternatively, or in conjunction, the treatment device may be used in situations where the sphincter fails to operate effectively, causing stomach acids to back up into the esophagus and irritating or degrading esophageal tissue. Disposing a treatment device including a flexible, silicone sleeve through the sphincter acts to protect sensitive esophageal tissue against such irritants.

Figure 5:
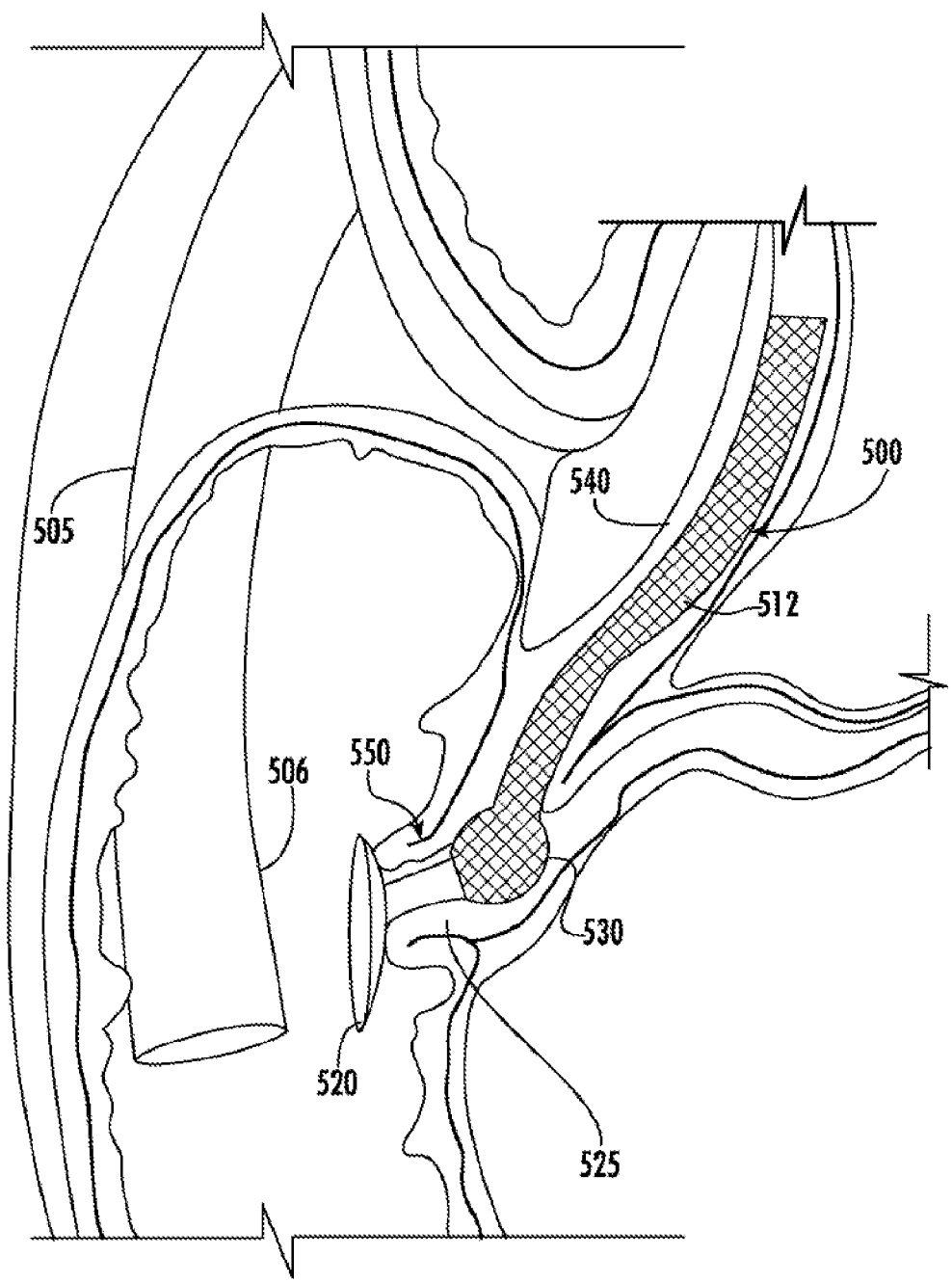
FIG. 5 illustrates one embodiment of a treatment device following deployment across a hepatopancreatic sphincter.

According to one aspect it is realized that the treatment device may be modified to improve stent efficacy through improved stent anchoring in a variety of applications. For example, FIG. 5 illustrates another application of a treatment device that incorporates a flexible sleeve anchor with a biliary stent. A biliary stent (also known as a "bile duct stent") is a flexible metallic tube designed to hold the bile duct open and may be inserted to address problems when the bile duct has been blocked or partially blocked. When a blockage occurs in the bile duct, fluids like bile (bilirubin) are unable to flow into the duodenum to aid in digestion.

In the embodiment of FIG. 5, the hepatopancreatic sphincter 550 of the Ampulla of Vater of may cooperate with an anchor sleeve 525 of a bile duct stent treatment device 500 to secure the treatment device 500 within the bile duct 540. The treatment device 500 is shown to include a proximal umbrella shaped flare 520, a flexible sleeve 525 and a distal bulb shaped flare 530 coupled to a treatment stent 512 configured to open the biliary passageway. As discussed previously, the shape of the flares 520, 530 are selected based upon the particular anatomy in which they are to be disposed, to suit the dual purpose of retaining the flare (and associated treatment device) without interfering with the function of the organ in which it is placed.

The treatment device 500 may be deployed from a window 506 of an endoscope 505, following advancement of the endoscope 505 into the duodenum. A delivery catheter may advance the treatment portion 512 of the device through the hepatopancreatic sphincter and into the bile duct 540 to restore bile duct operation. The device 500 may be advanced until the retention flare 530 is on a first side of the Ampulla of Vater, at which point the sleeve 525 may be released across the sphincter and the umbrella shaped flare 520 may be released into the duodenum, securing the sleeve within the sphincter and anchoring the treatment device 500 to the duct 540. In such embodiments, the flare diameters would be selected to extend 3-6 mm beyond the diameter of the treatment section 512 and the flexible sleeve 525, which may range from between 6-12 mm.

Figure 6:
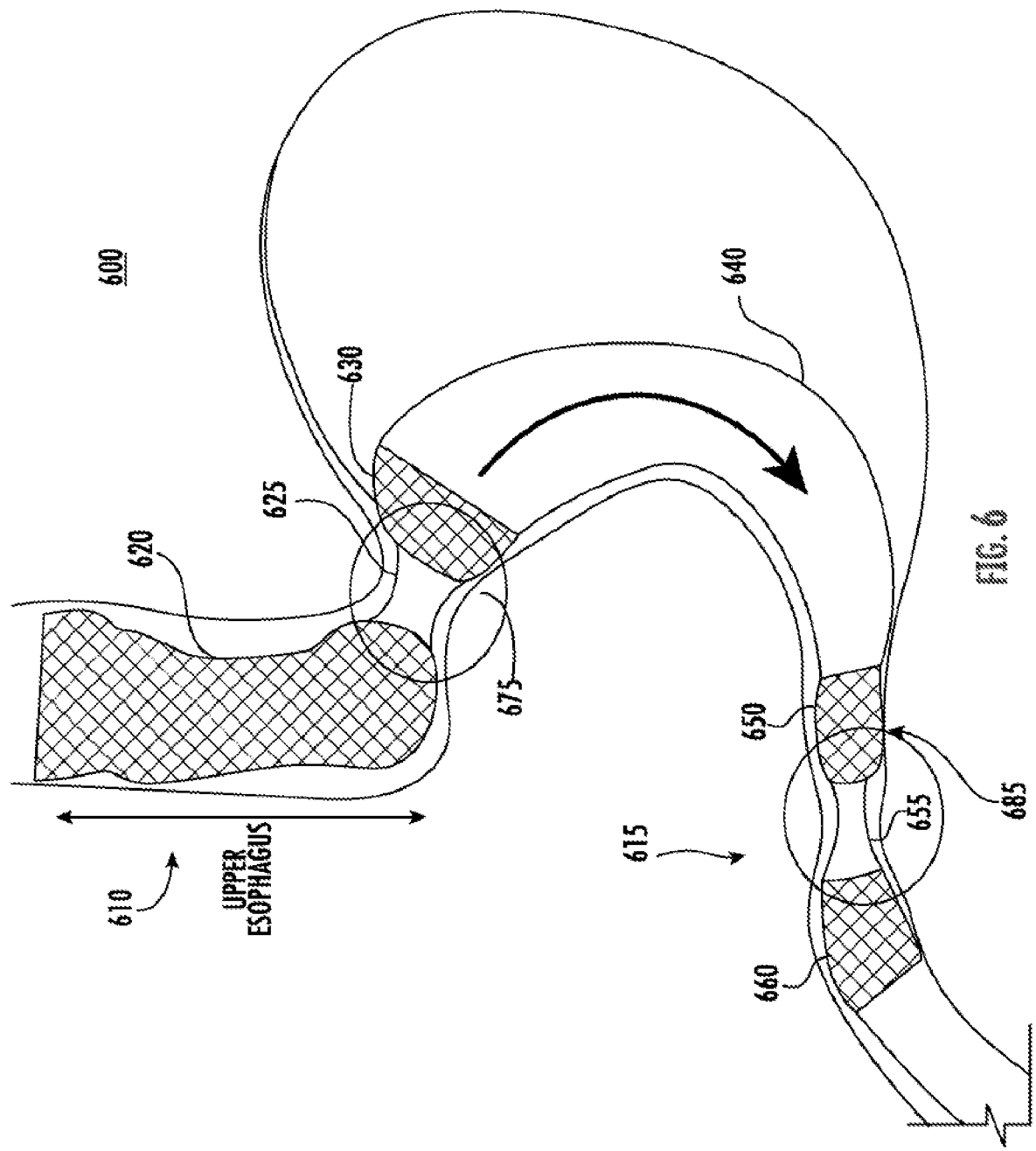
FIG. 6 illustrates one embodiment of a bypass system as disclosed in embodiments of the present disclosure.

FIG. 6 illustrates another application of a system, device and method using multiple anchoring stents to deliver a treatment along a gastrointestinal tract. For example, system 600 illustrates a non-invasive, reversible gastric bypass solution that leverages the constrictive mechanisms of the gastrointestinal tract to secure a barrier mechanism between the digestible material and the absorption anatomy (e.g., portions of the duodenum and/or jejunum of the small intestine). As used herein, "barrier" is intended to include impermeable, semi-permeable, and permeable walls, surfaces, membranes, etc., unless clearly indicated otherwise. A barrier may reduce or eliminate the need to alter anatomy of the patient via an invasive procedure. For example, a tubular barrier within a GI tract may allow passage of materials internally through the tubular barrier without significant (or substantially limited) contact with intestinal tissues and/or digestive enzymes or like fluids along the portion of the intestine occupied by the tubular barrier. Such restricted, limited, or delayed interaction between materials (e.g., stomach chyme) and the GI tract may assist with alleviating or at least positively impacting weight (obesity) and/or diabetic complications. Natural anatomy of the GI tract may be maintained while providing metabolic effects, e.g. prevention of fat and nutrient uptake throughout the length of the duodenum, without invasive surgery.

The system 600 includes a first treatment device 610, secured by the lower esophageal sphincter (LES) 675, and a second treatment device 615, secured by a pyloric sphincter 685. The first treatment device 610 and the second treatment device 615 may be coupled by a tubular barrier 640. In various embodiments the tubular barrier may comprise an elastic material such as silicone, polyethylene terephthalate (PET), nylon, rubber, a combination thereof, or the like. A tubular barrier may allow passage of materials through a lumen of the tubular barrier. Due to the malleability of a tubular barrier, smooth muscles may contract in peristaltic waves to translate materials through the tubular barrier. A tubular barrier may be permeable, allowing a portion of material through the barrier along the device. A permeability of a tubular barrier may be limited by a pore size that may allow passage of some materials while restricting others. A tubular barrier may include nanofibers that may increase rigidity and/or resilience of the tubular barrier compared to a barrier without fibers. The nanofibers may be oriented in patterns, e.g., crisscrossing, or the like.

The first treatment device 610 may comprise a proximal stent 620 coupled to a distal stent 630 via a flexible sleeve 625. As described above, the stent may be formed of a tubular scaffold made of nitinol or the like, and the sleeve may be formed of silicone. As described above, the proximal stent and/or distal stent may be constructed with one or more flares configured to aid in retention of the first treatment device within the esophagus. The distal stent 630 of the first treatment device may be glued, sewn or otherwise coupled to the tubular barrier 640.

The tubular barrier 640 may be coupled to a proximal stent 650 of the second treatment device 615, for example glued, sewn or otherwise attached. The proximal stent 650 of the second treatment device is shown further coupled to a flexible sleeve 655 and distal stent 660, where the proximal stent 650 and distal stent 660 help to secure the flexible sleeve 655 across the pyloric sphincter. In an exemplary embodiment, the system 600 may be deployed within a delivery catheter, first deploying the second treatment device 615 across the pyloric sphincter, then releasing the barrier 640 and subsequently deploying the first treatment device across the LES. Such an arrangement provides a non-invasive, secure, removable bypass mechanism that preserves patient anatomy.

Accordingly, a system and method for anchoring treatment devices leverages existing constriction musculature to improve treatment device retention. Such treatment devices may be used in a variety of applications including but not limited to treatment of esophageal strictures, gastrointestinal reflux and blocked biliary ducts, as well as to provide a non-invasive, anatomy preserving, reversible bypass solution.

The stents described in the various embodiments herein may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphtholate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the stents, and other components of the stents described herein, may also be doped with, made of, or otherwise include a radiopaque material. Radiopaque materials are understood to be materials capable of producing a relatively bright image on a fluoroscopy screen or another imaging technique during a medical procedure. This relatively bright image aids users in determining the stent's location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents to achieve the same result.

In some embodiments, a degree of Magnetic Resonance Imaging (MRI) compatibility is imparted into the stents described herein. For example, stents and other components of the stents, or portions thereof, may be made of a material that does not substantially distort the image and create substantial artifacts (e.g., gaps in the image). The stents may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method of deploying the treatment devices have been described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A device comprising an elongate tubular body configured for positioning across an anatomical constriction portion that regulates flow between a first anatomical flow path and a second anatomical flow path, the device comprising:
    a proximal stent having an elongate tubular wall having a proximal end, a distal end, a longitudinal extent therebetween the proximal end and the distal end configured to anchor the proximal stent with respect to anatomical structure proximal to the anatomical constriction portion, and a flare disposed at the distal end;
    a distal stent having an elongate tubular wall having a proximal end and a distal end and a longitudinal extent therebetween configured to anchor the distal stent with respect to anatomical structure distal to the anatomical constriction portion; and
    a sleeve more flexible than the proximal stent and the distal stent and coupled to the distal end of the proximal stent and the proximal end of the distal stent;
    wherein:
    the sleeve is configured to extend through and to conform to the anatomical constriction portion, and to transition in coordination with the anatomical constriction portion between an expanded configuration enabling flow through the sleeve and a constricted configuration wherein flow through the sleeve is restricted while the proximal stent remains anchored to anatomical structure proximal to the anatomical constriction portion and the distal stent remains anchored to anatomical structure distal to the anatomical constriction portion; and
    the proximal stent, the distal stent, and the sleeve together define a central lumen providing a flow path through the elongate tubular body resistant to migration.

2. The device of claim 1, wherein the device comprises an additional flare on at least one of the proximal stent or the distal stent.

3. The device of claim 2, wherein both the proximal stent and the distal stent each comprise at least one flare, wherein at least two of the flares have different diameters.

4. The device of claim 1, wherein the elongate tubular wall of the proximal stent and the elongate tubular wall of the distal stent each comprise a rigid or semi-rigid structure which is not pulled into the anatomical constriction portion as the flexible sleeve constricts with the anatomical constriction portion.

5. The device of claim 1, wherein the sleeve is formed of a material more flexible than the proximal stent and the distal stent to maintain efficacy of the anatomical constriction portion without causing the proximal stent and the distal stent to migrate.

6. The device of claim 5, wherein the proximal stent and the distal stent are configured to not be pulled into the anatomical constriction portion as the flexible sleeve constricts with the anatomical constriction portion.

7. The device of claim 1, wherein the sleeve has a length selected to extend between a proximal side of the anatomical constriction portion and the distal side of the anatomical constriction portion with the proximal stent affixed to tissue at the proximal side of the anatomical constriction portion, and the distal stent affixed to tissue at the distal side of the anatomical constriction portion.

8. The device of claim 1, wherein the sleeve is comprised of a material configured to transition from the expanded configuration to the constricted configuration in response to forces applied thereto by the anatomical constriction portion, thereby anchoring the device with respect to the anatomical constriction portion.

9. The device of claim 1, wherein:
the sleeve is configured to conform to an anatomical constriction portion comprising a sphincter;
the proximal stent is configured to engage tissue at a proximal end of the sphincter;
the distal stent is configured to engage tissue at a distal end of the sphincter; and
the sleeve is configured to transition from the expanded configuration when the sphincter is opened to the constricted configuration when the sphincter is closed, thereby maintaining sphincter efficacy, without affecting the positions of proximal stent and the distal stent surrounding and at each end of the sphincter.

10. The device of claim 9, wherein the sleeve is configured to move in coordination with the sphincter and to be compressed and anchored by the sphincter to secure the device against migratory forces resulting from the peristaltic motion of the sphincter.

11. The device of claim 1, wherein at least one of the proximal stent or the distal stent comprises one of a metal, a metal alloy, a polymer, a metal-polymer composite, a ceramic, or a combination thereof.

12. The device of claim 1, wherein the sleeve comprises a flexible silicone membrane.

13. The device of claim 1, wherein the sleeve comprises a tube having one of a fixed or variable thickness, ranging from between 20 microns and 150 microns.

14. The device of claim 1, wherein at least one of the proximal stent or the distal stent comprises a treatment portion comprising one of a tubular scaffold, a coating, a mesh or combination thereof.

15. A system including:
a first elongate body positioned across a first anatomical constriction portion and comprising:
a first tubular wall defining a proximal retention end of the first elongate body and extending longitudinally to define an elongate exterior configured to anchor with respect to an anatomical structure proximal to the first anatomical constriction portion;
a second tubular wall defining a distal retention end of the first elongate body and extending longitudinally to define an elongate exterior configured to anchor with respect to an anatomical structure distal to the first anatomical constriction portion; and
a flexible sleeve coupled between the first tubular wall and the second tubular wall;
wherein:
the flexible sleeve is configured to extend across the first anatomical constriction portion to transition in coordination with application of a retention force from the first anatomical constriction portion on the flexible sleeve between an expanded configuration enabling flow through the flexible sleeve when the first anatomical constriction portion is open and a constricted configuration when the first anatomical constriction portion constricts;
the first tubular wall and the second tubular wall are configured to be anchored to anatomical structure on either side of the first anatomical constriction portion across which the flexible sleeve therebetween extends;
the first tubular wall and the second tubular wall and the flexible sleeve cooperate with the first anatomical constriction portion to retain the first elongate body in place with respect to the first anatomical constriction portion; and
the first tubular wall includes a flare disposed adjacent the flexible sleeve, the flexible sleeve extending distally from the flare.

16. The system of claim 15, further comprising:
a second elongate body positioned across a second anatomical constriction portion and comprising:
a first tubular wall defining a proximal retention end of the second elongate body and extending longitudinally to define an elongate exterior configured to anchor with respect to an anatomical structure proximal to the second anatomical constriction portion;
a second tubular wall defining a distal retention end of the second elongate body and extending longitudinally to define an elongate exterior configured to anchor with respect to an anatomical structure distal to the second anatomical constriction portion; and
a flexible sleeve coupled between the first tubular wall and the second tubular wall; and
a bypass sleeve coupling the second tubular wall of the first elongate body and the first tubular wall of the second elongate body.

17. The system of claim 16, wherein the length of the bypass sleeve is selected to extend between an esophageal sphincter and a pyloric sphincter.

18. The system of claim 15, wherein the first elongate body comprises an additional flare on at least one of the first tubular wall or the second tubular wall.

19. The system of claim 15, wherein the flexible sleeve comprises a material different from a material of either the first tubular wall or the second tubular wall.

20. A method of anchoring a stent using a feature of a body lumen, the method comprising:
deploying an elongate structure into a body lumen, wherein at least a portion of the body lumen is configured to constrict and expand, the elongate structure comprising a flexible sleeve configured to inhibit affixation of the flexible sleeve with tissue of the body lumen, a proximal stent coupled to a proximal end of the flexible sleeve, and a distal stent coupled to a distal end of the flexible sleeve;
releasing the distal stent from a delivery catheter to engage an elongated tubular wall of the distal stent with a body lumen wall proximate and distal to the portion of the body lumen that constricts and expands;
releasing the flexible sleeve from the delivery catheter to extend within the portion of the body lumen that constricts and expands; and
releasing the proximal stent from the delivery catheter to engage an elongated tubular wall of the distal stent with a body lumen wall proximate and distal to the portion of the body lumen that constricts and expands;
wherein a proximal end of the flexible sleeve is coupled to a flare at a distal end of the proximal stent, and a distal end of the flexible sleeve is coupled to at least a portion of the distal stent, and the flexible sleeve is configured to constrict and expand in coordination with the portion of the body lumen that constricts and expands, enabling retention of the proximal stent and the distal stent proximate to, without being pulled into, the portion of the body lumen that constricts and expands.

\* \* \* \* \*